US010817621B2

(12) United States Patent
Takahashi et al.

(10) Patent No.: US 10,817,621 B2
(45) Date of Patent: Oct. 27, 2020

(54) ANONYMIZATION PROCESSING DEVICE, ANONYMIZATION PROCESSING METHOD, AND PROGRAM

(71) Applicant: NTT PC Communications Incorporated, Minato-ku (JP)

(72) Inventors: Keisuke Takahashi, Minato-ku (JP); Kosuke Yabuki, Minato-ku (JP); Yusuke Kumihashi, Minato-ku (JP)

(73) Assignee: NTT PC Communications Incorporated, Minato-ku (JP)

( * ) Notice: Subject to any disclaimer, the term of this patent is extended or adjusted under 35 U.S.C. 154(b) by 137 days.

(21) Appl. No.: 15/545,834

(22) PCT Filed: Jan. 12, 2016

(86) PCT No.: PCT/JP2016/050737
§ 371 (c)(1),
(2) Date: Jul. 24, 2017

(87) PCT Pub. No.: WO2016/121493
PCT Pub. Date: Aug. 4, 2016

(65) Prior Publication Data
US 2018/0012039 A1    Jan. 11, 2018

(30) Foreign Application Priority Data

Jan. 27, 2015  (JP) ................................ 2015-013504

(51) Int. Cl.
*G06F 21/64* (2013.01)
*G06F 17/30* (2006.01)
(Continued)

(52) U.S. Cl.
CPC ........ *G06F 21/6254* (2013.01); *G06F 16/285* (2019.01); *G06F 21/62* (2013.01); *G06N 20/00* (2019.01); *G06Q 50/22* (2013.01)

(58) Field of Classification Search
None
See application file for complete search history.

(56) References Cited

U.S. PATENT DOCUMENTS

2003/0208457 A1    11/2003  Iyengar
2004/0199781 A1*   10/2004  Erickson ............. G06F 21/6254
                                                                726/26
(Continued)

FOREIGN PATENT DOCUMENTS

EP     2 228 735 A2    9/2010
JP     2012/150651 A   8/2012
(Continued)

OTHER PUBLICATIONS

CN102867022. English Translation. Univ Shanghai Jiaotong. (Year: 2015).*

(Continued)

*Primary Examiner* — Venkat Perungavoor
(74) *Attorney, Agent, or Firm* — Oblon, McClelland, Maier & Neustadt, L.L.P.

(57) ABSTRACT

An anonymization processing device is provided that anonymizes input data and outputs anonymized output data. The device receives the input data, anonymizes the input data, to generate anonymized data corresponding to the input data, and stores the anonymized data in a first memory. When a plurality of anonymized data items stored in the memory satisfy an anonymity index, the device generates and output a plurality of output data items corresponding to the anonymized data items, respectively, and deletes the anonymized data items from the first memory. The device further generates a plurality of the anonymization patterns based on the anonymized data items, stores the anonymization patterns in a second memory, and when the information items included in the anonymized data stored in the first memory is equivalent to each of the information items included in the (Continued)

anonymization pattern, respectively, the device outputs the output data from the anonymized data.

6 Claims, 21 Drawing Sheets

(51) Int. Cl.
*G06F 21/62* (2013.01)
*G06N 20/00* (2019.01)
*G06F 16/28* (2019.01)
*G06Q 50/22* (2018.01)
*G06F 21/78* (2013.01)

(56) References Cited

U.S. PATENT DOCUMENTS

| | | | |
|---|---|---|---|
| 2006/0059196 A1* | 3/2006 | Sato | H04L 45/54 |
| 2010/0169332 A1* | 7/2010 | Bezzi | G06F 16/24 |
| | | | 707/757 |
| 2012/0197915 A1* | 8/2012 | Miyakawa | G06Q 10/00 |
| | | | 707/755 |
| 2014/0122442 A1* | 5/2014 | Takenouchi | G06F 21/556 |
| | | | 707/687 |
| 2014/0172854 A1* | 6/2014 | Huang | G06F 21/6245 |
| | | | 707/737 |
| 2015/0006512 A1* | 1/2015 | Alfonseca | G06F 40/258 |
| | | | 707/722 |
| 2015/0007249 A1* | 1/2015 | Bezzi | G06F 21/6254 |
| | | | 726/1 |
| 2015/0286841 A1* | 10/2015 | Takenouchi | G06F 16/2228 |
| | | | 726/26 |
| 2015/0339488 A1* | 11/2015 | Takahashi | G06F 21/6218 |
| | | | 726/29 |
| 2015/0363601 A1* | 12/2015 | Kamishiro | G06F 3/1222 |
| | | | 726/26 |
| 2016/0196453 A1* | 7/2016 | Yamaoka | G06F 21/6254 |
| | | | 726/26 |

FOREIGN PATENT DOCUMENTS

| | | |
|---|---|---|
| JP | 2014-153943 A | 8/2014 |
| JP | 2014-164477 A | 9/2014 |

OTHER PUBLICATIONS

KANIS: Preserving k-Anonymity Over Distributed Data. Doka et al. ACM. (Year: 2011).*
A Fuzzy Variant of k-Member Clustering for Collaborative Filtering With Data Anonymization. Honda. IEEE. (Year: 2012).*
Automatic Privacy Query Updation for Moving Objects. Madhavi. IJESAT. (Year: 2012).*
International Search Report dated Mar. 22, 2016 in PCT/JP2016/050737 filed Jan. 12, 2016.
Guo, Kun et al., "Fast clustering-based anonymization approaches with time constraints for data streams," Knowledge Based Systems, 2013, pp. 95-108.
Cao, Jianneng et al., "CASTLE: Continuously Anonymizing Data Streams," IEEE Transactions on Dependable and Secure Computing, vol. 8, No. 3, 2011, pp. 337-352.
Extended European Search Report dated Oct. 24, 2018 in Patent Application No. 16743097.4, 7 pages.

* cited by examiner

FIG.4A k-ANONYMITY INDEX VALUE

| k | 3 |
|---|---|

FIG.4B

REAL-TIME DEFINITION INFORMATION

| RETENTION TERM | 3 HOURS |
|---|---|

FIG.4C

ANONYMITY DETERMINATION INFORMATION

| NAME |
|---|
| AGE |
| PRESENT ADDRESS |
| SEX |
| RECEPTION DATE |
| ATTENDING-DOCTOR ID |

OUTPUT OBJECT INFORMATION

| RECORD ID |
| AGE |
| PRESENT ADDRESS |
| SEX |
| RECEPTION DATE |
| MEDICAL DEPARTMENT |
| SYMPTOMS |

FIG.6A

DATA BEFORE ANONYMIZATION

| RECORD ID | NAME | AGE | PRESENT ADDRESS | SEX | RECEPTION DATE | MEDICAL DEPARTMENT | ATTENDING-DOCTOR ID | SYMPTOMS |
|---|---|---|---|---|---|---|---|---|
| A101 | SUZUKI DAISUKE | 42 | 1-11-101 1-CHOME XY ADACHI, TOKYO | MALE | 2014/7/1 | INTERNAL MEDICINE | 1234 | HEADACHE |

FIG.6B

ANONYMIZATION PROCESS MANAGEMENT INFORMATION

| RECORD ID | RECORD ID OF DATA BEFORE ANONYMIZATION | RECORD ID OF DATA AFTER ANONYMIZATION | ANONY-MIZATION METHOD SETTING FLAG | ANONY-MIZATION METHOD | ANONY-MIZATION LEVEL | ANONY-MIZATION SETTING FLAG | GENERA-TION DATE AND TIME |
|---|---|---|---|---|---|---|---|
| K101 | A101 | NULL | FALSE | NULL | NULL | FALSE | 2015/1/1 12:25:30 |

FIG.10A

DATA AFTER ANONYMIZATION

| RECORD ID | NAME | AGE | PRESENT ADDRESS | SEX | RECEPTION DATE | MEDICAL DEPART-MENT | ATTEND-ING-DOCTOR ID | SYMP-TOMS |
|---|---|---|---|---|---|---|---|---|
| B101 | NULL | FOR-TIES | ADACHI, TOKYO | FE-MALE | JULY, 2014 | INTER-NAL MEDI-CINE | NULL | HEAD-ACHE |

FIG.10B

ANONYMIZATION PROCESS MANAGEMENT INFORMATION

| RECORD ID | RECORD ID OF DATA BEFORE ANONYMIZATION | RECORD ID OF DATA AFTER ANONYMIZATION | ANONYMIZATION METHOD SETTING FLAG | ANONYMIZATION METHOD | ANONYMIZATION LEVEL | ANONYMIZATION SETTING FLAG | GENERATION DATE AND TIME |
|---|---|---|---|---|---|---|---|
| K101 | A101 | B101 | TRUE | | | TRUE | 2015/1/1 12:25:30 |

| ANONYMIZATION METHOD | ANONYMIZATION LEVEL |
|---|---|
| {"NAME": "REMOVE", "AGE": "GENERALIZE", "PRESENT ADDRESS": "GENERALIZE", "SEX": "RANDOMIZE", "RECEPTION DATE": "GENERALIZE", "MEDICAL DEPARTMENT": "NO PROCESS", "ATTENDING-DOCTOR ID": "REMOVE", "SYMPTOMS": "NO PROCESS"} | {"AGE": "CHANGE ONE'S DIGIT TO 0 TO CLASSIFY BY DECADES", "PRESENT ADDRESS": "DELETE CITY, WARD, TOWN, VILLAGE, AND FURTHER DETAILS", "SEX": "RANDOMIZE ASSUMING RATIO OF MALE TO FEMALE BEING 103:100", "RECEPTION DATE": "DELETE DAY OF THE MONTH"} |

FIG.12A

DATA AFTER ANONYMIZATION (OBJECT OF OUTPUT DETERMINATION)

| RECORD ID | NAME | AGE | PRESENT ADDRESS | SEX | RECEPTION DATE | MEDICAL DEPARTMENT | ATTEND-ING-DOCTOR ID | SYMPTOMS |
|---|---|---|---|---|---|---|---|---|
| B101 | NULL | FOR-TIES | ADACHI, TOKYO | FEMALE | JULY, 2014 | INTERNAL MEDICINE | NULL | HEADACHE |

FIG.12B

DATA AFTER ANONYMIZATION (EXISTING IN DB OF DATA BEFORE ANONYMIZATION)

| RECORD ID | NAME | AGE | PRESENT ADDRESS | SEX | RECEPTION DATE | MEDICAL DEPART- MENT | ATTEND- ING- DOCTOR ID | SYMP- TOMS |
|---|---|---|---|---|---|---|---|---|
| B95 | NULL | FOR- TIES | ADACHI, TOKYO | FEMALE | JULY, 2014 | INTERNAL MEDICINE | NULL | HEAD- ACHE |
| B97 | NULL | FOR- TIES | ADACHI, TOKYO | FEMALE | JULY, 2014 | CARDIOL- OGY | NULL | SHORT- NESS OF BREATH |
| B99 | NULL | FOR- TIES | ADACHI, TOKYO | FEMALE | JULY, 2014 | INTERNAL MEDICINE | NULL | COUGH |

FIG.12C

OUTPUT DATA

| RECORD ID | AGE | PRESENT ADDRESS | SEX | RECEPTION DATE | MEDICAL DEPARTMENT | SYMPTOMS |
|---|---|---|---|---|---|---|
| B95 | FORTIES | ADACHI, TOKYO | FEMALE | JULY, 2014 | INTERNAL MEDICINE | HEADACHE |
| B97 | FORTIES | ADACHI, TOKYO | FEMALE | JULY, 2014 | CARDIOLOGY | SHORT BREATH |
| B99 | FORTIES | ADACHI, TOKYO | FEMALE | JULY, 2014 | INTERNAL MEDICINE | COUGH |
| B101 | FORTIES | ADACHI, TOKYO | FEMALE | JULY, 2014 | INTERNAL MEDICINE | HEADACHE |

FIG.12D

ANONYMIZATION PATTERN DATA

| RECORD ID | NAME | AGE | PRESENT ADDRESS | SEX | RECEPTION DATE | ATTEND-ING-DOCTOR ID |
|---|---|---|---|---|---|---|
| T1 | NULL | FOR-TIES | ADACHI, TOKYO | FEMALE | JULY, 2014 | NULL |

FIG.12E

DATA AFTER ANONYMIZATION (OBJECT OF OUTPUT DETERMINATION)

| RECORD ID | NAME | AGE | PRESENT ADDRESS | SEX | RECEPTION DATE | MEDICAL DEPARTMENT | ATTENDING-DOCTOR ID | SYMPTOMS |
|---|---|---|---|---|---|---|---|---|
| B151 | NULL | FORTIES | ADACHI, TOKYO | FEMALE | JULY, 2014 | INTERNAL MEDICINE | NULL | HEADACHE |

FIG.12F

OUTPUT DATA

| RECORD ID | AGE | PRESENT ADDRESS | SEX | RECEPTION DATE | MEDICAL DEPARTMENT | SYMPTOMS |
|---|---|---|---|---|---|---|
| B150 | FOR-TIES | ADACHI, TOKYO | FEMALE | JULY, 2014 | INTERNAL MEDICINE | HEAD-ACHE |

TEACHER DATA

| RECORD ID | NAME | AGE | PRESENT ADDRESS | SEX | RECEPTION DATE | MEDICAL DEPART-MENT | ATTENDING-DOCTOR ID | SYMP-TOMS |
|---|---|---|---|---|---|---|---|---|
| A101 | SUZUKI DAISUKE | 42 | 1-11-101 1-CHOME XY ADACHI, TOKYO | MALE | 2014/7/1 | INTERNAL MEDICINE | 1234 | HEAD-ACHE |

| RECORD ID OF DATA BEFORE ANONYMIZATION | RECORD ID OF DATA AFTER ANONYMIZATION | ANONYMIZATION METHOD SETTING FLAG | ANONYMIZATION METHOD | ANONYMIZATION LEVEL | ANONYMIZATION SETTING FLAG | k-ANONYMITY CRITERION CONFORMITY FLAG | GENERATION DATE AND TIME |
|---|---|---|---|---|---|---|---|
| A101 | B101 | TRUE | | | TRUE | FALSE | 2015/1/1 12:25:30 |
| K101 | | | | | | | |

| ANONYMIZATION METHOD | ANONYMIZATION LEVEL |
|---|---|
| {"NAME": "REMOVE", "AGE": "GENERALIZE", "PRESENT ADDRESS": "GENERALIZE", "SEX": "RANDOMIZE", "RECEPTION DATE": "GENERALIZE", "MEDICAL DEPARTMENT": "NO PROCESS", "ATTENDING-DOCTOR ID": "REMOVE", "SYMPTOMS": "NO PROCESS"} | {"AGE": "CHANGE ONE'S DIGIT TO 0 TO CLASSIFY BY DECADES", "PRESENT ADDRESS": "DELETE CITY, WARD, TOWN, VILLAGE, AND FURTHER DETAILS", "SEX": "RANDOMIZE ASSUMING RATIO OF MALE TO FEMALE BEING 103:100", "RECEPTION DATE": "DELETE DAY OF THE MONTH"} |

FIG.13A

TEACHER DATA

| RECORD ID | NAME | AGE | PRESENT ADDRESS | SEX | RECEPTION DATE | MEDICAL DEPARTMENT | ATTENDING-DOCTOR ID | SYMPTOMS |
|---|---|---|---|---|---|---|---|---|
| A101 | SUZUKI DAISUKE | 42 | 1-11-101 1-CHOME XY ADACHI, TOKYO | MALE | 2014/7/1 | INTERNAL MEDICINE | 1234 | HEADACHE |

| RECORD ID OF DATA BEFORE ANONYMIZATION | RECORD ID OF DATA AFTER ANONYMIZATION | ANONYMIZATION METHOD | ANONYMIZATION LEVEL | ANONYMIZATION METHOD SETTING FLAG | ANONYMIZATION SETTING FLAG | k-ANONYMITY CRITERION CONFORMITY FLAG | GENERATION DATE AND TIME |
|---|---|---|---|---|---|---|---|
| A101 | B101 | | | TRUE | | | |
| | K101 | | | | TRUE | TRUE | 2015/1/1 12:25:30 |

ANONYMIZATION METHOD:

{"NAME": "REMOVE",
"AGE": "GENERALIZE",
"PRESENT ADDRESS": "GENERALIZE",
"SEX": "RANDOMIZE",
"RECEPTION DATE": "GENERALIZE",
"MEDICAL DEPARTMENT": "NO PROCESS",
"ATTENDING-DOCTOR ID": "REMOVE",
"SYMPTOMS": "NO PROCESS"}

ANONYMIZATION LEVEL:

["AGE": "CHANGE ONE'S DIGIT TO 0 TO CLASSIFY BY DECADES",
"PRESENT ADDRESS": "DELETE CITY, WARD, TOWN, VILLAGE, AND FURTHER DETAILS",
"SEX": "RANDOMIZE ASSUMING RATIO OF MALE TO FEMALE BEING 103:100",
"RECEPTION DATE": "DELETE DAY OF THE MONTH"}

FIG.13B

ANONYMIZATION PROCESSING DEVICE, ANONYMIZATION PROCESSING METHOD, AND PROGRAM

TECHNICAL FIELD

The present invention relates to an anonymization processing device, an anonymization processing method, and a program.

BACKGROUND ART

In recent years, as can be seen in recommendation technologies, technologies have been progressing that analyze a large amount of personal information to utilize information obtained from analysis results in various ways. Also, anonymization technologies have been known that enable to execute data analysis while protecting individual privacy.

Such a conventional anonymization technology deletes predetermined specific columns in personal information records in a database that stores a large amount of personal information, by batch processing, to execute an anonymization process.

RELATED ART DOCUMENTS

Non-Patent Documents

Patent document 1: Japanese Unexamined Patent Application Publication No. 2014-153943

SUMMARY OF INVENTION

Problem to be Solved by the Invention

However, since the conventional anonymization technology executes an anonymization process by batch processing, it is difficult to use the anonymization technology in a real-time operation system into which data is input continuously.

The disclosed technology has been made in view of the above, and has an object to provide a technology that can anonymize data being input continuously while maintaining a real-time property.

Means for Solving the Problem

According to the disclosed technology, an anonymization processing device that anonymizes input data and outputs anonymized output data, includes an input unit configured to receive the input data; a processing unit configured to anonymize the input data, to generate anonymized data corresponding to the input data that has been anonymized; a first storage unit configured to store the anonymized data; and an output unit configured, in a case where a plurality of anonymized data items stored in the first storage unit satisfy an anonymity index, to generate and output a plurality of output data items corresponding to the anonymized data items, respectively, and to delete the anonymized data items from the first storage unit.

Advantage of the Invention

According to the disclosed technology, it is possible to provide a technology that can anonymize data being input continuously while maintaining a real-time property.

BRIEF DESCRIPTION OF DRAWINGS

FIG. 4A is a diagram illustrating an example of setting information;

FIG. 4B is a diagram illustrating an example of setting information;

FIG. 4C is a diagram illustrating an example of setting information;

FIG. 6A is a diagram illustrating an example of data before anonymization, and anonymization process management information;

FIG. 6B is a diagram illustrating an example of data before anonymization, and anonymization process management information;

FIG. 10A is a diagram illustrating an example of data after anonymization, and anonymization process management information;

FIG. 10B is a diagram illustrating an example of data after anonymization, and anonymization process management information;

FIG. 12A is a diagram illustrating an example of various data items input and output by a process executed by an output determination unit;

FIG. 12B is a diagram illustrating an example of various data items input and output by a process executed by an output determination unit;

FIG. 12C is a diagram illustrating an example of various data items input and output by a process executed by an output determination unit;

FIG. 12D is a diagram illustrating an example of various data items input and output by a process executed by an output determination unit;

FIG. 12E is a diagram illustrating an example of various data items input and output by a process executed by an output determination unit;

FIG. 12F is a diagram illustrating an example of various data items input and output by a process executed by an output determination unit;

FIG. 13A is a diagram illustrating an example of teacher data;

FIG. 13B is a diagram illustrating an example of teacher data; and

EMBODIMENTS OF THE INVENTION

Figure 1:
FIG. 1 is a diagram illustrating an overview of an anonymization processing device according to an embodiment.

In the following, embodiments will be described with reference to the drawings. In the drawings, identical elements are assigned the same codes, and duplicate description may be omitted.

<Overview>

FIG. 1 is a diagram illustrating an overview of an anonymization processing device according to an embodiment. The anonymization processing device 10 receives input data including personal information from an external system or the like, and applies an anonymization process to the received input data. Also, the anonymization processing device 10 outputs anonymized data (output data) to the external system or the like.

Here, "anonymization" means a data processing method that makes it difficult to identify an individual person, by removing personally identifiable information in personal information (removal); probabilistically changing the personally identifiable information (randomization); and lowering precision of the personally identifiable information (generalization). Also, as an index to evaluate anonymity (anonymity index), k-anonymity has been known. The "k-anonymity" represents a state where k or more persons exist having similar attributes. For example, if ten persons exist having the addresses located "Minato-ku, Tokyo" and having the ages of "thirties", the anonymity of this data is represented as "k=10". In other words, the greater the value of k is, the more persons exist having similar attributes, which makes it difficult to identify the individuals (the anonymity increases).

In order to anonymize input data in real time, the anonymization processing device 10 temporarily stores the input data and the anonymized data in an in-memory database, and if the anonymized data satisfies the k-anonymity, outputs the anonymized data to the external system or the like.

Also, unlike a system that stores all input data in a database and executes anonymization by batch processing at a later timing, the anonymization processing device 10 aims at anonymizing data while maintaining real-timeliness. Therefore, if the anonymized data cannot be output instantly (e.g., if the anonymized data does not satisfy the k-anonymity within a predetermined time, or if the number of records accumulated into the in-memory database exceeds a predetermined threshold), the anonymization processing device 10 deletes such anonymized data from the in-memory database without outputting the anonymized data to the external system or the like because the freshness of the data has dropped.

Also, the anonymization processing device 10 anonymizes input data, based on information representing which of the anonymization methods (removal, randomization, and generalization) is used for the anonymization, and on information representing a degree of anonymization for each of the anonymization methods. Also, the anonymization processing device 10 has a function of an on-line machine learning framework that learns an evaluation result (teacher data) representing whether the anonymized data satisfies an anonymity index, or the anonymized data does not satisfy the anonymity index, to adjust a degree of generalization (may be referred to as the "degree of generalization", below) when the personally identifiable information is to be generalized.

Note that although the present embodiment will be described assuming that data input into the anonymization processing device 10 is personal information managed in a hospital or the like, the anonymization processing device 10 according to the present embodiment can also be applied to a system managing other types of personal information.

Note that in the present embodiment, although the anonymization processing device 10 uses an in-memory database in order to raise the processing speed, another database may be used.

Note that in the present embodiment, although the anonymization processing device 10 uses the k-anonymity as the anonymity index, another type of anonymity index may be used.

Note that in the present embodiment, although the anonymization processing device 10 uses removal, randomization, and generalization as the anonymization methods, it is not limited to these anonymization methods; other anonymization methods may be used.

<Hardware Configuration>

Figure 2:
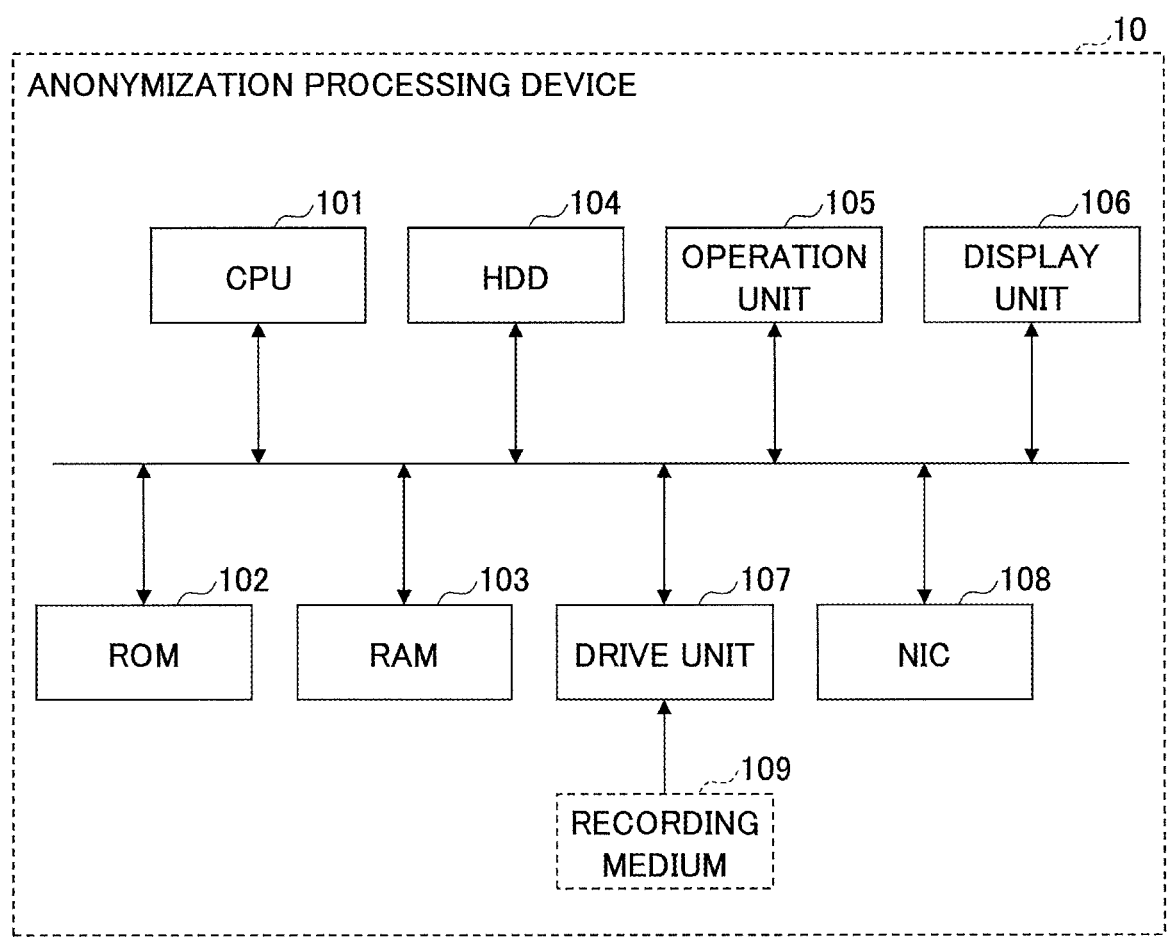
FIG. 2 is a diagram illustrating an example of a hardware configuration of an anonymization processing device according to an embodiment.

FIG. 2 is a diagram illustrating an example of a hardware configuration of the anonymization processing device according to the embodiment. The anonymization processing device 10 according to the embodiment has a CPU 101, a ROM 102, a RAM 103, an HDD 104, an operation unit 105, a display unit 106, a drive unit 107, and a NIC (Network Interface Card) 108.

The CPU 101 is a processor to execute overall control of the anonymization processing device 10. The CPU 101 runs programs stored in the HDD 104 or the like, such as an operating system, applications, and various services, to implement various functions of the anonymization processing device 10. The ROM 102 stores various programs, data used by the programs, and the like. The RAM 103 is used as a memory area for loading a program, a work area of the loaded program, and the like. Also, the RAM 103 retains an in-memory database used when executing an anonymization process. The HDD 104 stores various information items, programs, and the like.

The operation unit 105 is hardware for receiving input operations from a user, for example, a keyboard or a mouse. The display unit 106 is hardware to execute displaying for the user.

The drive unit 107 reads a program from a recording medium 109 that records the program. The program read by the drive unit 107 is installed, for example, in the HDD 104. The NIC 108 is a communication interface for connecting the anonymization processing device 10 to a network, and transmitting and receiving data.

Note that the recording medium 109 means a non-transitory recording medium. Examples of the recording medium 109 include a magnetic recording medium, an optical disc, a magneto-optic recording medium, and a non-volatile memory.

<Software Configuration>

Figure 3:
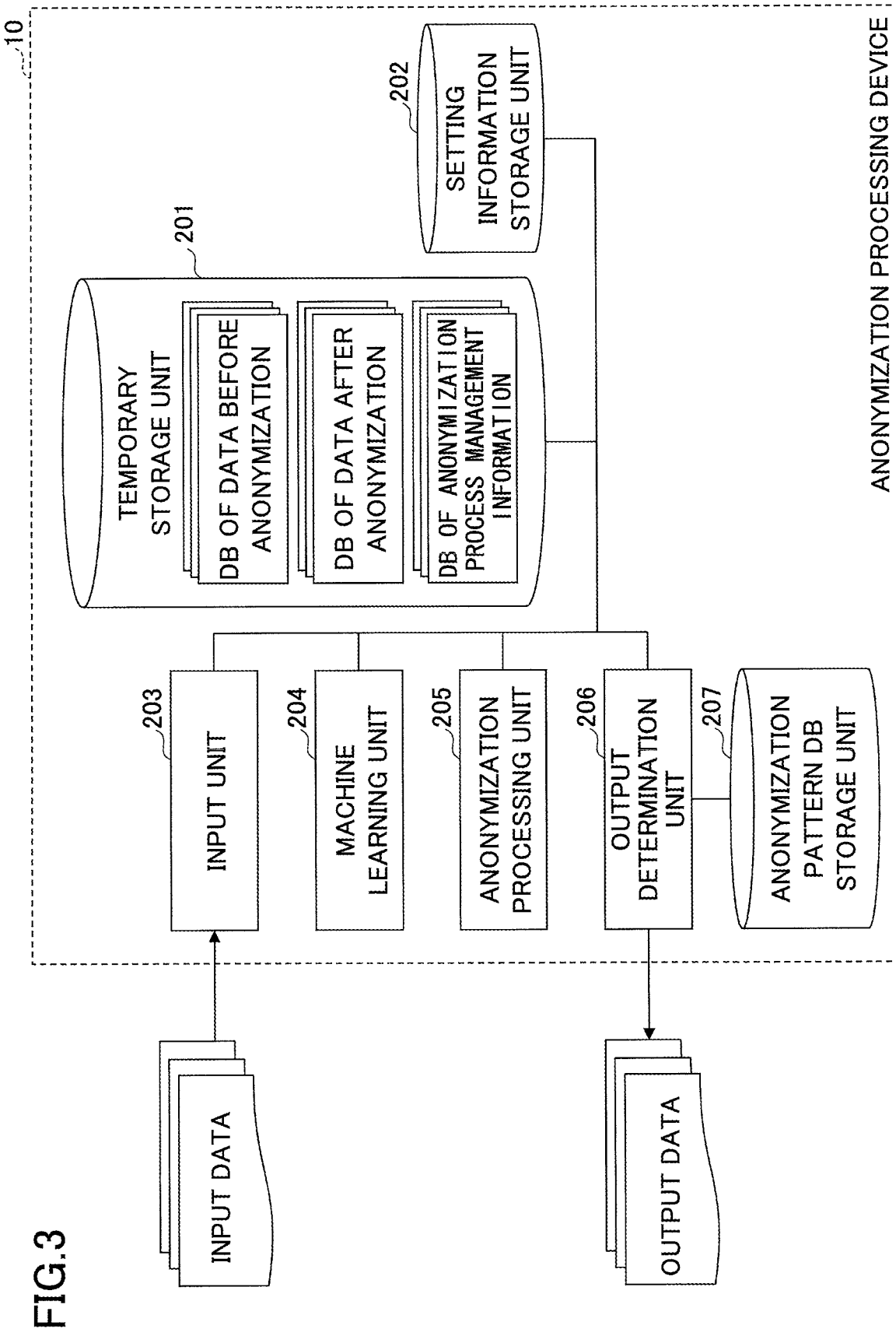
FIG. 3 is a diagram illustrating an example of a software configuration of an anonymization processing device according to an embodiment.

FIG. 3 is a diagram illustrating an example of a software configuration of the anonymization processing device according to the embodiment. The anonymization processing device 10 according to the embodiment has a temporary storage unit 201, a setting information storage unit 202, an input unit 203, a machine learning unit 204, an anonymization processing unit 205, an output determination unit 206, and an anonymization pattern DB storage unit 207. These units may be implemented by processes executed by the CPU 101 running one or more programs installed in the anonymization processing device 10.

The temporary storage unit 201 has a DB (Database) of data before anonymization, a DB of data after anonymization, and a DB of anonymization process management information. The DB of data before anonymization is a DB to store data before anonymization (data before the anonymization process is applied), storing an item of data before anonymization per record. The DB of data after anonymization is a DB to store data after anonymization (data after the anonymization process has been applied), storing an item of data after anonymization per record. The DB of anonymization process management information stores an item of anonymization process management information per record. The anonymization process management information includes information to have the data before anonymization associated with the data after anonymization, and to represent the state of progress of an anonymization process and the anonymization method and the anonymization level. The temporary storage unit 201 is implemented by the in-memory database built in the RAM 103. Note that the temporary storage unit 201 may be implemented by a generic database built in the HDD 104 and the like, instead of the RAM 103.

The setting information storage unit 202 stores various setting information items relating to operations of the anonymization processing device 10. The input unit 203, the machine learning unit 204, the anonymization processing unit 205, and the output determination unit 206 can refer to the various setting information items stored in the setting information storage unit 202 when necessary.

The input unit 203 receives input data from the external system or the like, adds a new record into the DB of data before anonymization, and stores the received input data in the added record. The input unit 203 also adds a new record into the DB of anonymization process management information corresponding to the generated record.

The machine learning unit 204 stores, based on a learning result by teacher data, information of anonymization methods representing how to anonymize data before anonymization, and information representing the anonymization level for each anonymization method, in the DB of anonymization process management information. Also, based on teacher data received from the external device or teacher data received from the output determination unit 206, the machine learning unit 204 adjusts the degree of generalization. If having adjusted the degree of generalization, the machine learning unit 204 indicates this adjustment to the anonymization processing unit 205 by an RPC (Remote Procedure Call).

Based on the anonymization process management information corresponding to the data before anonymization, the anonymization processing unit 205 executes an anonymization process for the data before anonymization, adds a new record into the DB of data after anonymization, and stores the anonymized data in the added record. Also, if having received an indication of a changed degree of generalization from the machine learning unit 204, the anonymization processing unit 205 executes an anonymization process again for the data to which the anonymization process has been already applied.

Also, if the data after anonymization cannot satisfy the k-anonymity within a predetermined time, or if the number of records accumulated in the temporary storage unit 201 exceeds a predetermined threshold, the anonymization processing unit 205 deletes the data before anonymization, the data after anonymization, and the anonymization process management information from the temporary storage unit 201, in order from oldest date and time of generation, which will be described later.

The output determination unit 206 searches for the data after anonymization stored in the DB of data after anonymization, to determine whether the data after anonymization satisfies the k-anonymity, or whether the data after anonymization matches an anonymization pattern stored in the anonymization pattern DB storage unit 207. If the data after anonymization satisfies the k-anonymity, or the data after anonymization matches an anonymization pattern, the output determination unit 206 determines that the data after anonymization satisfies the anonymity index, and outputs the data after anonymization as output data. Also, the output determination unit 206 deletes the data before anonymization, the data after anonymization, and the anonymization process management information that correspond to the output data, from the temporary storage unit 201.

Alternatively, if the data after anonymization does not satisfy the k-anonymity, and the data after anonymization does not match an anonymization pattern, the output determination unit 206 determines that the data after anonymization does not satisfy the anonymity index, and leaves the data after anonymization in the DB of data after anonymization, without outputting as output data.

Also, the output determination unit 206 indicates a determination result representing whether the anonymity index is satisfied or is not satisfied to the machine learning unit 204, as teacher data.

The anonymization pattern DB storage unit 207 stores one or more anonymization patterns. The anonymization pattern DB is generated from data after anonymization that has been determined to satisfy the anonymity index in the past. In other words, the anonymization pattern DB is a database of patterns that satisfy the anonymity index. It is possible for the output determination unit 206 to determine whether data after anonymization satisfies the anonymity index, by simply confirming whether the data after anonymization matches an anonymization pattern by using the anonymization pattern DB.

FIGS. 4A-4D are diagrams illustrating examples of setting information. The anonymization processing device 10 according to the embodiment has, as setting information, a k-anonymity index value, real-time definition information, anonymity determination information, and output object information. These setting information items are stored in the setting information storage unit 202.

The k-anonymity index value is a specific number of "k" used for determination of the k-anonymity. The real-time definition information is information stored in the DB of data before anonymization and the DB of data after anonymization, defining a retention term (a lifetime) of the data before anonymization and the data after anonymization. The anonymity determination information is information that represents which columns among various columns included in data after anonymization are referred to by the output determination unit 206 to determine the anonymity. The output object information is information that represents which columns among various columns included in data after anonymization are output as output data. The output determination unit 206 extracts the columns represented in the output object information among the data after anonymization, to generate the output data.

<Processing Steps>
(Input Data Storing Process)

Figures 4D, 5:
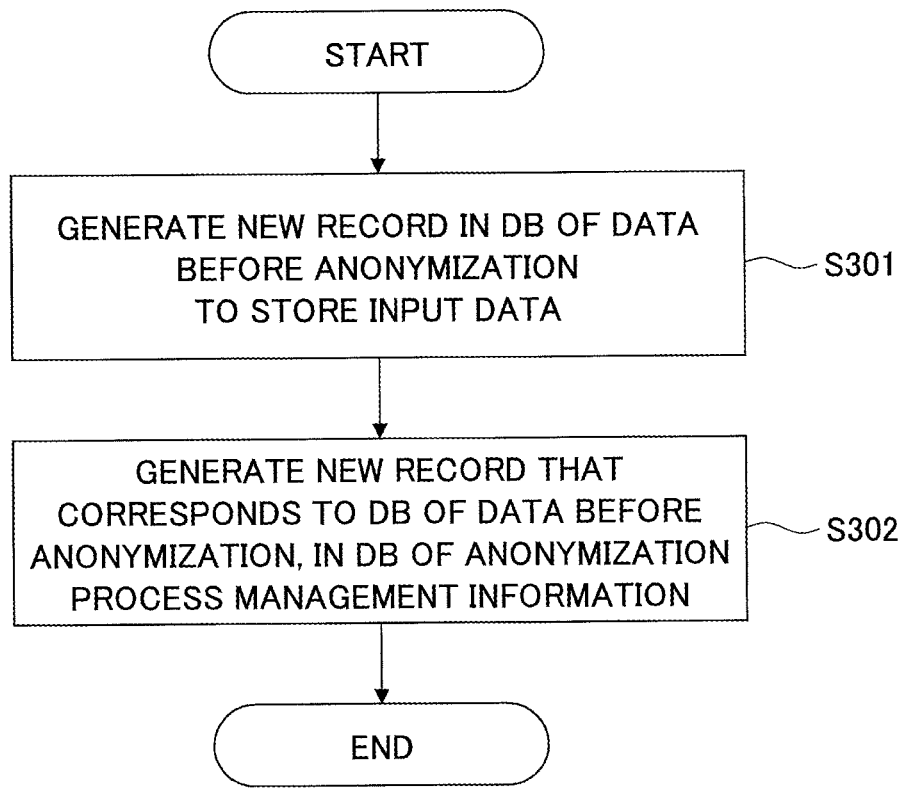
FIG. 4D is a diagram illustrating an example of setting information.
FIG. 5 is a diagram illustrating an example of processing steps of an input data storing process.

FIG. 5 is a diagram illustrating an example of processing steps of an input data storing process. FIGS. 6A-6B are diagrams illustrating examples of data before anonymization, and anonymization process management information. Using FIG. 5 and FIGS. 6A-6B, processing steps will be described in which input data is input into the input unit 203, and stored in the temporary storage unit 201.

At Step S301, upon receiving input data from the external system or the like, the input unit 203 generates a new record in the DB of data before anonymization, and stores a record ID for uniquely identifying the record in the DB of data before anonymization. Also, the input unit 203 stores the input data in the new record. FIG. 6A is an example of data before anonymization added to the DB of data before anonymization by the input unit 203. The data before anonymization has multiple columns (record ID, name, age, present address, sex, reception date, medical department, attending-doctor ID, and symptoms).

At Step S302, the input unit 203 generates a new record in the DB of anonymization process management information, and stores a record ID for uniquely identifying the record in the DB of anonymization process management information. The input unit 203 stores in the new record the record ID of the data before anonymization generated at the processing step of Step S301, and the date and time when the data before anonymization was generated at the processing step of Step S301. FIG. 6B is an example of anonymization process management information added to the DB of anonymization process management information by the input unit 203. The anonymization process management information has multiple columns (record ID, record ID of data before anonymization, record ID of data after anonymization, anonymization method setting flag, anonymization method, anonymization level, anonymization setting flag, and generation date and time). The record ID of data after anonymization, the anonymization method setting flag, the anonymization method, the anonymization level, and the anonymization setting flag are columns used when the machine learning unit 204, the anonymization processing unit 205, and the output determination unit 206 execute processing, and hence, are set to "NULL" or "FALSE". The generation date and time column is a column to store the date and time when the data before anonymization was generated.

The input unit 203 repeatedly executes the processing steps of Step S301 and Step S302 to store input data items in the temporary storage unit 201 one by one.

(Setting Process of Anonymization Method and Anonymization Level)

Figure 7:
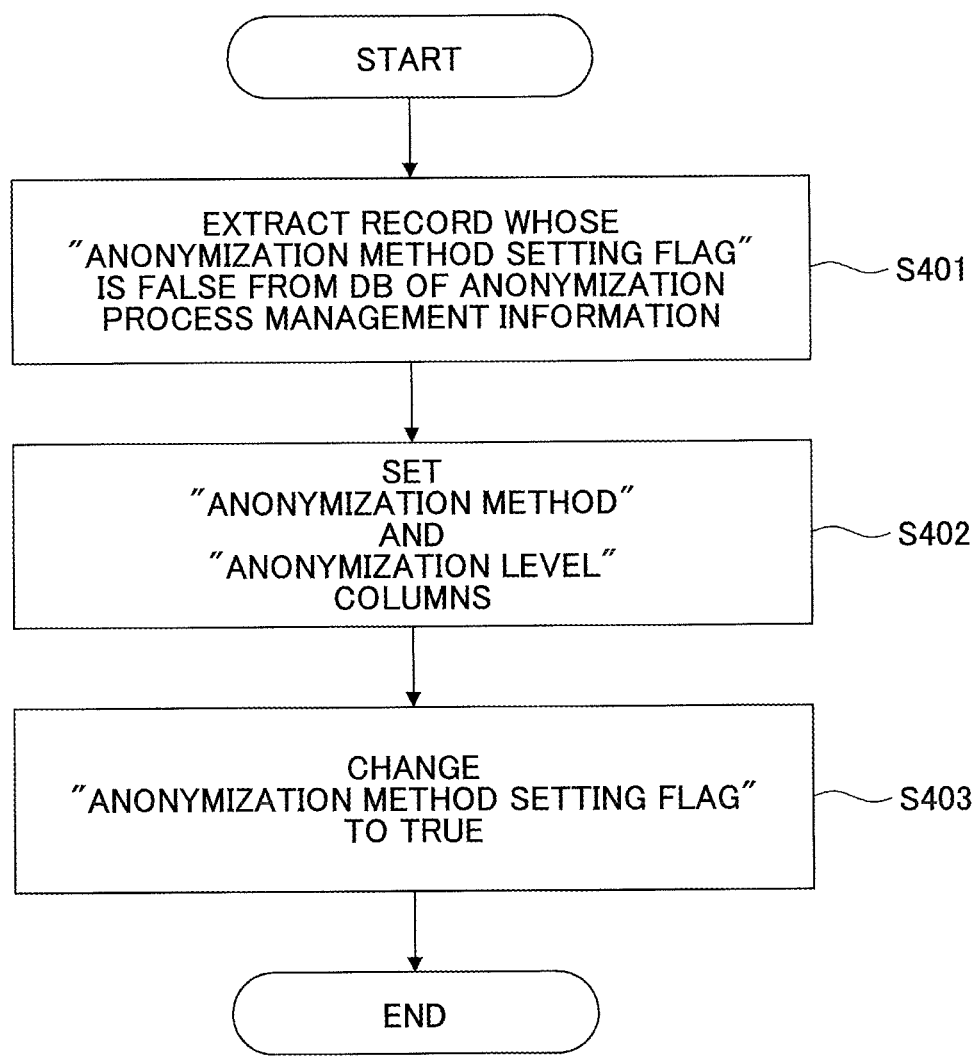
FIG. 7 is a diagram illustrating an example of processing steps for setting an anonymization method and an anonymization level.
Figure 8:
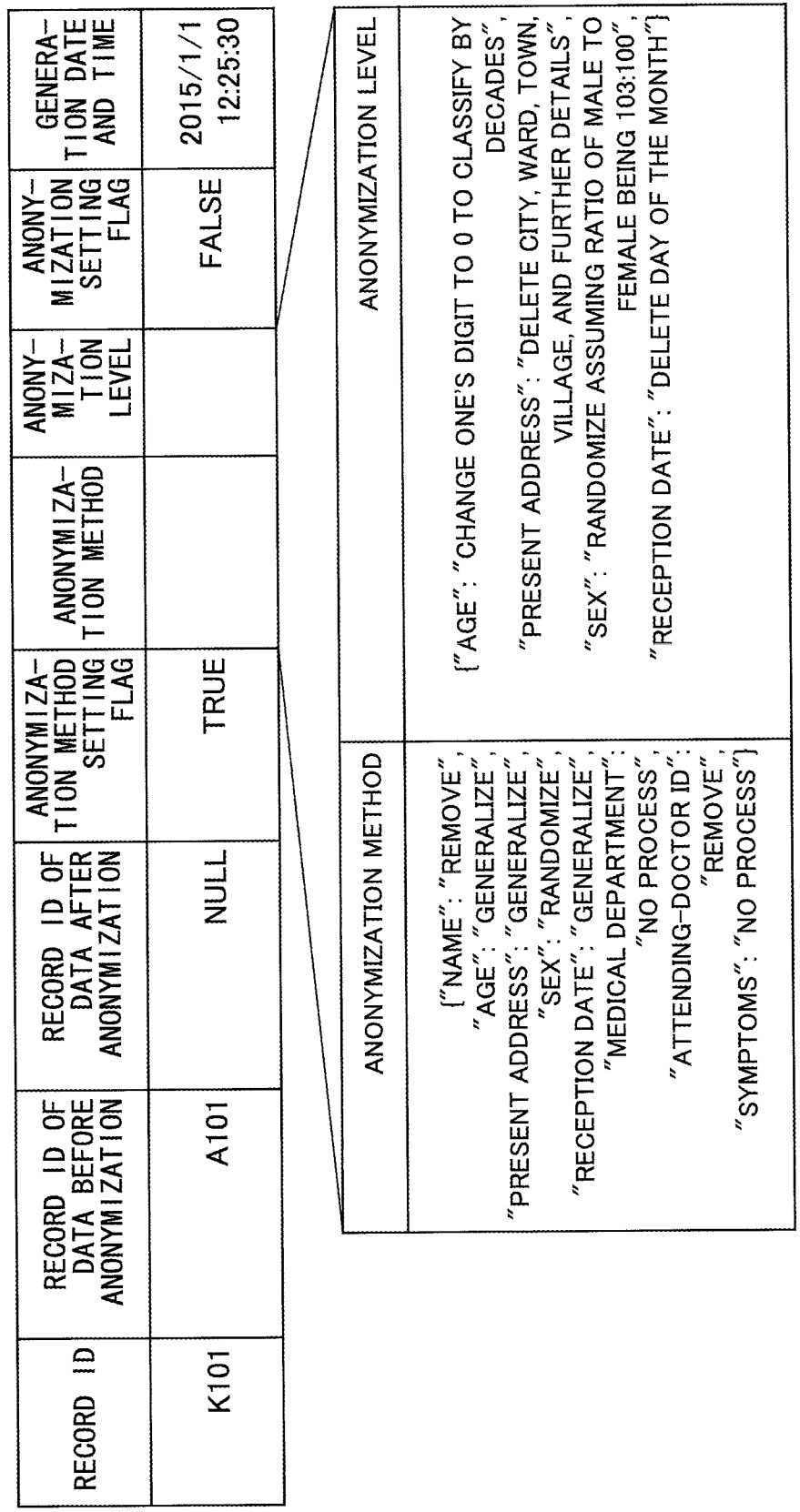
FIG. 8 is a diagram illustrating an example of anonymization process management information in which an anonymization method and an anonymization level have been set.

FIG. 7 is a diagram illustrating an example of processing steps for setting an anonymization method and an anonymization level. FIG. 8 is a diagram illustrating an example of anonymization process management information in which an anonymization method and an anonymization level have been set. Using FIG. 7 and FIG. 8, processing steps will be described in which the machine learning unit 204 sets an anonymization method and an anonymization level in anonymization process management information.

At Step S401, the machine learning unit 204 searches in the DB of anonymization process management information, to extract all records whose "anonymization method setting flag" is FALSE. Here, the anonymization method setting flag is a flag representing whether the machine learning unit 204 has already executed settings of the anonymization method and the anonymization level. If the "anonymization method setting flag" is "FALSE", the flag represents a state where the machine learning unit 204 has not yet executed settings of the anonymization method and the anonymization level; or if the "anonymization method setting flag" is "TRUE", the flag represents a state where the machine learning unit 204 has already executed settings of the anonymization method and the anonymization level.

At Step S402, the machine learning unit 204 sets an anonymization method and an anonymization level into the "anonymization method" and "anonymization level" columns of each record extracted at the processing step of Step S401. Here, in the "anonymization method" column, information is stored that represents which columns are to be anonymized by which of the anonymization methods. Also, in the "anonymization level" column, information is stored that represents what ratio of randomization is to be executed in the case of using randomization, or to what extent generalization is to be executed in the case of using generalization. The anonymization process management information illustrated in FIG. 8 is an example of anonymization process management information in which the "anonymization method" and "anonymization level" columns have been set by the machine learning unit 204. The anonymization process management information in FIG. 8 represents that the data before anonymization designated by the "record ID of data before anonymization" column is to be anonymized such that the "name" column is removed; the "age" is generalized by changing the last digit to 0; the "present address" column is generalized by deleting city, ward, town, village, and further details; the "sex" column is randomized assuming the ratio of male to female being 103:100; the "reception date" column is generalized by deleting the day of the month; the "attending-doctor ID" column is removed; and the "medical department" column and the "symptoms" column are left as they are.

Note that if multiple records have been extracted at the processing step of Step S401, the machine learning unit 204 executes Step S402 for all the records.

(Anonymization Process)

Figure 9:
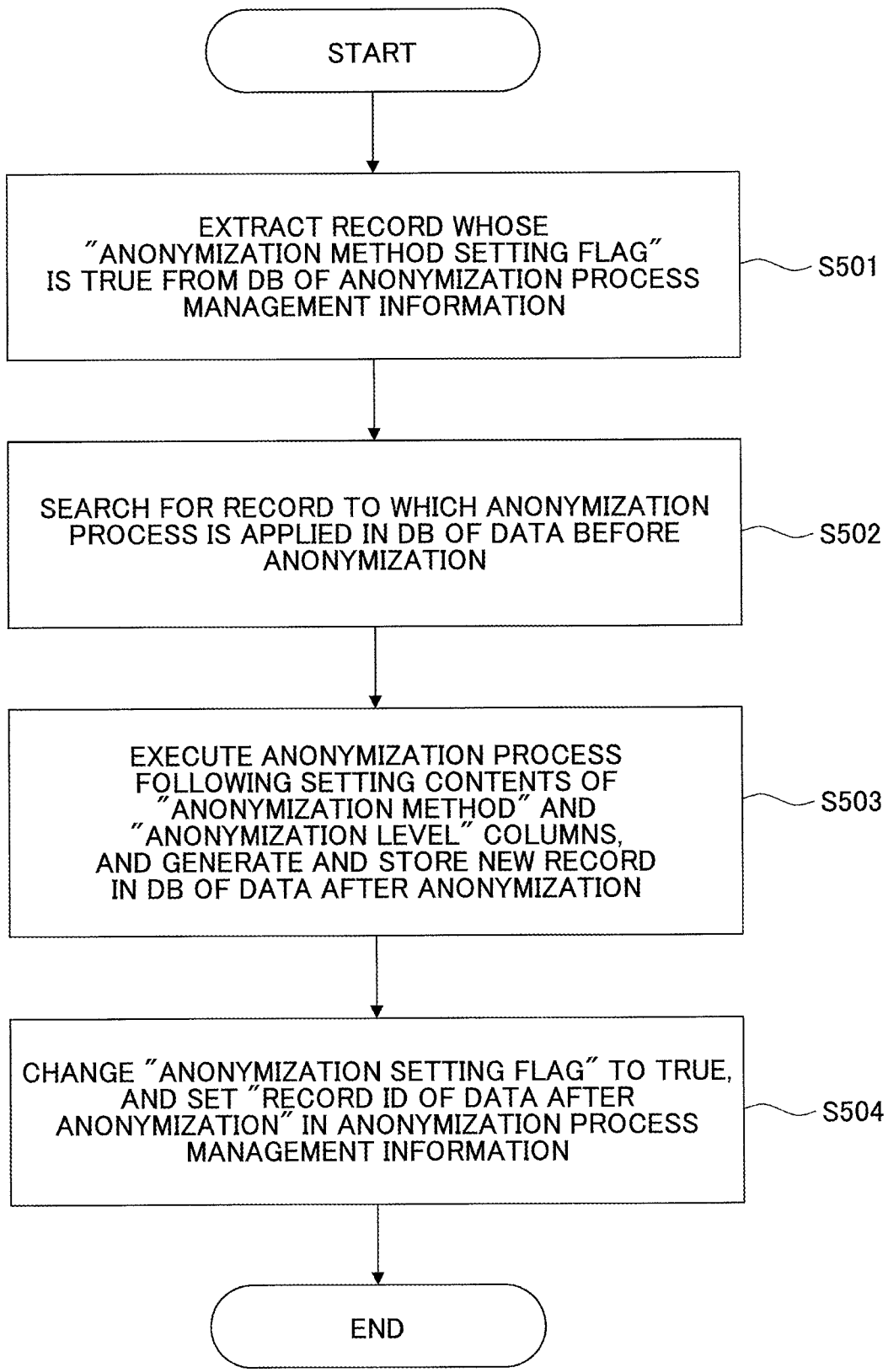
FIG. 9 is a diagram illustrating an example of processing steps of an anonymization process.

FIG. 9 is a diagram illustrating an example of processing steps of an anonymization process. FIGS. 10A-10B are diagrams illustrating examples of data after anonymization, and anonymization process management information. Using FIG. 9 and FIGS. 10A-10B, processing steps will be described in which the anonymization processing unit 205 executes an anonymization process based on the anonymization process management information.

At Step S501, the anonymization processing unit 205 extracts all records whose "anonymization method setting flag" columns are TRUE from the DB of anonymization process management information.

At Step S502, the anonymization processing unit 205 searches in the DB of data before anonymization for data before anonymization corresponding to the records extracted at the processing step of Step S501.

At Step S503, the anonymization processing unit 205 anonymizes the data before anonymization found at Step S502, following the setting contents of the "anonymization method" and "anonymization level" columns in the anonymization process information corresponding to the data before anonymization, and generates and stores a new record in the DB of data after anonymization. FIG. 10A illustrates a specific example of data after anonymization stored in the DB of data after anonymization. The data before anonymization found at the processing step of Step S502 is the data before anonymization illustrated in FIG. 6A, and if the anonymization process information corresponding to the data before anonymization is the anonymization process information illustrated in FIG. 8, the data before anonymization is anonymized as in FIG. 10A.

At Step S504, the anonymization processing unit 205 changes the "anonymization setting flag" column of the anonymization process information into TRUE, and stores the record ID of the data after anonymization stored in the DB of data after anonymization at the processing step of Step S503, in the "record ID of data after anonymization" column.

Note that if multiple records have been extracted at the processing step of Step S501, the anonymization processing unit 205 executes the processing steps of Step S502 through Step S504 to all the records.

(Output Process)

Figure 11:
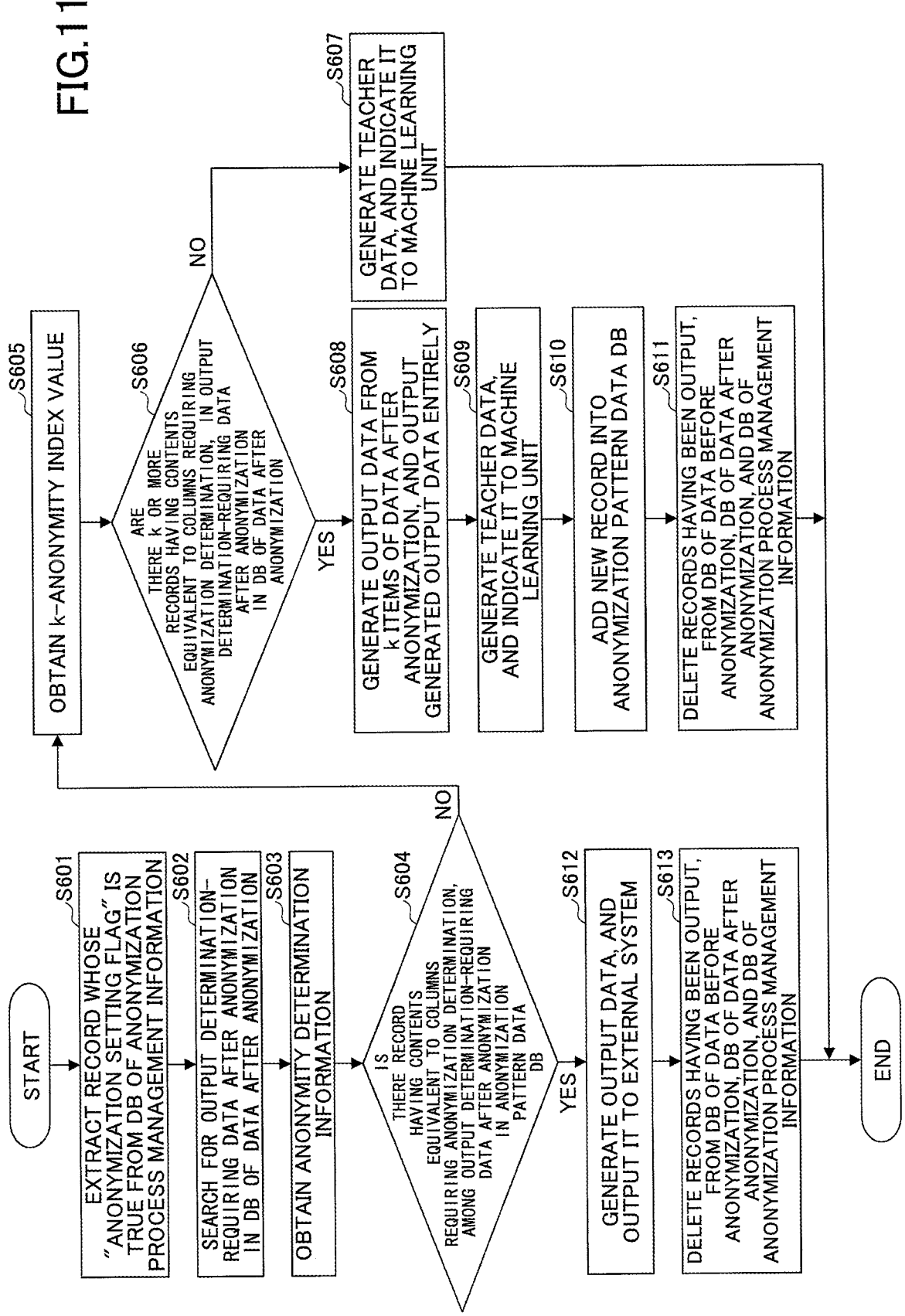
FIG. 11 is a diagram illustrating an example of processing steps of an output process.

FIG. 11 is a diagram illustrating an example of processing steps of an output process. FIGS. 12A-12F are diagrams illustrating examples of various data items input and output by a process executed by the output determination unit. FIGS. 13A-13B are diagrams illustrating examples of teacher data. Using FIG. 11 to FIG. 13, processing steps will be described in which output data is output based on data after anonymization.

At Step S601, the output determination unit 206 extracts all records whose "anonymization setting flag" column is TRUE from the anonymization process information DB.

At Step S602, the output determination unit 206 searches in the DB of data after anonymization for data after anonymization corresponding to the records extracted at the processing step of Step S601.

At Step S603, the output determination unit 206 obtains the anonymity determination information from the setting information storage unit 202.

At Step S604, the output determination unit 206 selects, among the columns of the data after anonymization found at the processing step of Step S602 (referred to as the "output determination-requiring data after anonymization"), columns that have been set in the anonymity determination information (referred to as the "columns requiring anonymization determination"), and confirms whether a record having the same contents as in all the selected columns, exists in the anonymization pattern DB. If a record having the same contents as in all the selected columns exists in the anonymization pattern DB, the output determination unit 206 determines that the output determination-requiring data after anonymization satisfies the k-anonymity, and proceeds to the processing step of Step S612. If a record having the same contents as in all the selected columns, does not exist in the anonymization pattern DB, the output determination unit 206 proceeds to the processing step of Step S605.

Here, specific examples will be described using FIGS. 12A-12F. Assume that data after anonymization illustrated in FIG. 12A is output determination-requiring data after anonymization, and an anonymization pattern illustrated in FIG. 12D is included in the anonymization pattern DB. Assume also that the columns illustrated in FIG. 4C ("name", "age", "present address", "sex", "reception date", and "attending-doctor ID") are set in the anonymity determination information.

The output determination unit 206 selects columns requiring anonymization determination among the columns included in the output determination-requiring data after anonymization illustrated in FIG. 12A, and confirms whether a record having the same setting values as the setting values of these columns exists in the anonymization pattern DB. The setting values of the columns requiring anonymization determination of the output determination-requiring data after anonymization in FIG. 12A are the same as the setting values of the columns of the anonymization pattern illustrated in FIG. 12D. Therefore, the output determination unit 206 determines that the output determination-requiring data after anonymization satisfies the k-anonymity, and proceeds to the processing step of Step S612.

Referring back to FIG. 11, description will continue. At Step S605, the output determination unit 206 obtains the k-anonymity index value from the setting information storage unit 202.

At Step S606, the output determination unit 206 selects columns requiring anonymization determination among the columns of the output determination-requiring data after anonymization, and confirms whether k or more records having contents equivalent to the selected columns exist in the DB of data after anonymization. If k or more records exist, the output determination unit 206 determines that the output determination-requiring data after anonymization satisfies the k-anonymity, and proceeds to the processing step of Step S608; or if k or more records do not exist, the output determination unit 206 determines that the output determination-requiring data after anonymization does not satisfy the k-anonymity, and proceeds to the processing step of Step S607.

Here, specific examples will be described using FIGS. 12A-12F. Assume that data after anonymization illustrated in FIG. 12A is output determination-requiring data after anonymization, and three items of data after anonymization illustrated in FIG. 12B exist in the DB of data after anonymization. Assume also that the k-anonymity index value is "3", and the columns illustrated in FIG. 4C are set in the anonymity determination information.

The output determination unit 206 selects columns requiring anonymization determination among the columns included in the output determination-requiring data after anonymization illustrated in FIG. 12A, and confirms whether a record having the same setting values as the setting values of these columns exists in the DB of data after anonymization. The three items of data after anonymization illustrated in FIG. 12B have the same setting values of the columns requiring anonymization determination as the setting values of the columns of the output determination-requiring data after anonymization. Therefore, the output determination unit 206 determines that the output determination-requiring data after anonymization satisfies the k-anonymity, and proceeds to the processing step of Step S608.

Suppose that if the record having the record ID of B95 did not exist in the DB of data after anonymization among FIG. 12B, only two records exist in the DB of data after anonymization that have the same contents as the columns requiring anonymization determination, among the columns of the output determination-requiring data after anonymization. Therefore, the output determination unit 206 determines that the output determination-requiring data after anonymization does not satisfy the k-anonymity, and proceeds to the processing step of Step S607.

Referring back to FIG. 11, description will continue. At Step S607, the output determination unit 206 generates teacher data from the data before anonymization corresponding to the output determination-requiring data after anonymization, and the anonymization process management information, and indicates the generated teacher data to the machine learning unit 204. FIG. 13A is an example of teacher data generated at the processing step of Step S607. The teacher data is data that includes the anonymity determination information having the "k-anonymity criterion conformity flag" column added, and the data before anonymization. The "k-anonymity criterion conformity flag" is a flag that represents whether the data after anonymization satisfies the k-anonymity. If it is determined that the data after anonymization satisfies the k-anonymity, TRUE is set to the "k-anonymity criterion conformity flag" of the teacher data; or if it is determined that k-anonymity is not satisfied, FALSE is set to the "k-anonymity criterion conformity flag" of the teacher data. When generating teacher data at the processing step of Step S607, the output determination unit

206 sets the "k-anonymity criterion conformity flag" column to FALSE. This is because it has been determined at the processing step of Step S606 that the output determination-requiring data after anonymization does not satisfy the k-anonymity.

At Step S608, the output determination unit 206 obtains the output object information from the setting information storage unit 202. Next, the output determination unit 206 generates the output data from the k items of the data after anonymization, and the output determination-requiring data after anonymization, and outputs the generated output data to the external system or the like. Note that the output determination unit 206 generates the output data by extracting the columns set in the output object information, from the columns of the data after anonymization.

Here, specific examples will be described using FIGS. 12A-12F. Assume that data after anonymization illustrated in FIG. 12A is output determination-requiring data after anonymization, and three items of data after anonymization illustrated in FIG. 12B exist in the DB of data after anonymization. Assume also that k-anonymity index value is "3", and the columns illustrated in FIG. 4D are set in the output object information ("record ID", "age", "present address", "sex", the "reception date", the "medical department", "symptoms"). In this case, the output data output at the processing step of Step S608 consists of four items, which are the output data illustrated in FIG. 12C.

Referring back to FIG. 11, description will continue. At Step S609, the output determination unit 206 selects one item of the data after anonymization among k items of the data after anonymization, generates teacher data from the data before anonymization corresponding to the selected data after anonymization, and the anonymization process management information, and indicates the generated teacher data to the machine learning unit 204. FIG. 13B is a specific example of teacher data generated at the processing step of Step S609. When generating teacher data at the processing step of Step S607, the output determination unit 206 sets the "k-anonymity criterion conformity flag" column to TRUE. This is because it has been determined at the processing step of Step S606 that the output determination-requiring data after anonymization satisfies the k-anonymity.

At Step S610, the output determination unit 206 selects one item of the data after anonymization among k items of the data after anonymization, and extracts the columns requiring anonymization determination from the selected data after anonymization. Also, the output determination unit 206 generates an anonymization pattern from the extracted columns, and adds and stores a new record in the anonymization patterns. For example, assuming that output data output at Step S608 is the four items in FIG. 12C, the anonymization pattern illustrated in FIG. 12D is generated.

At Step S611, the output determination unit 206 deletes the data before anonymization, the data after anonymization, and the anonymization process management information corresponding to k items of the output data output at Step S608, from the DB of data before anonymization, the DB of data after anonymization, and the DB of anonymization process management information, respectively.

At Step S612, the output determination unit 206 obtains the output object information from the setting information storage unit 202. Next, the output determination unit 206 extracts the columns set in the output object information from the columns of the data after anonymization determined to exist in the anonymization pattern DB, to generate the output data. Next, the output determination unit 206 outputs the generated output data to the external system or the like.

Here, specific examples will be described using FIGS. 12A-12F. Assume that the output determination-requiring data after anonymization is represented by data after anonymization illustrated in FIG. 12E, and the columns illustrated in FIG. 4D are set in the output object information. In this case, the output data output at the processing step of Step S612 is output data illustrated in FIG. 12F.

Referring back to FIG. 11, description will continue. At Step S613, the output determination unit 206 deletes the data before anonymization, the data after anonymization, and the anonymization process management information corresponding to the output data output at Step S612, from the DB of data before anonymization, the DB of data after anonymization, and the DB of anonymization process management information, respectively.

Note that if multiple records have been extracted at the processing step of Step S601, the output determination unit 206 executes the processing steps of Step S602 through Step S613 to all the records.

(Reprocessing Steps)

Figure 14:
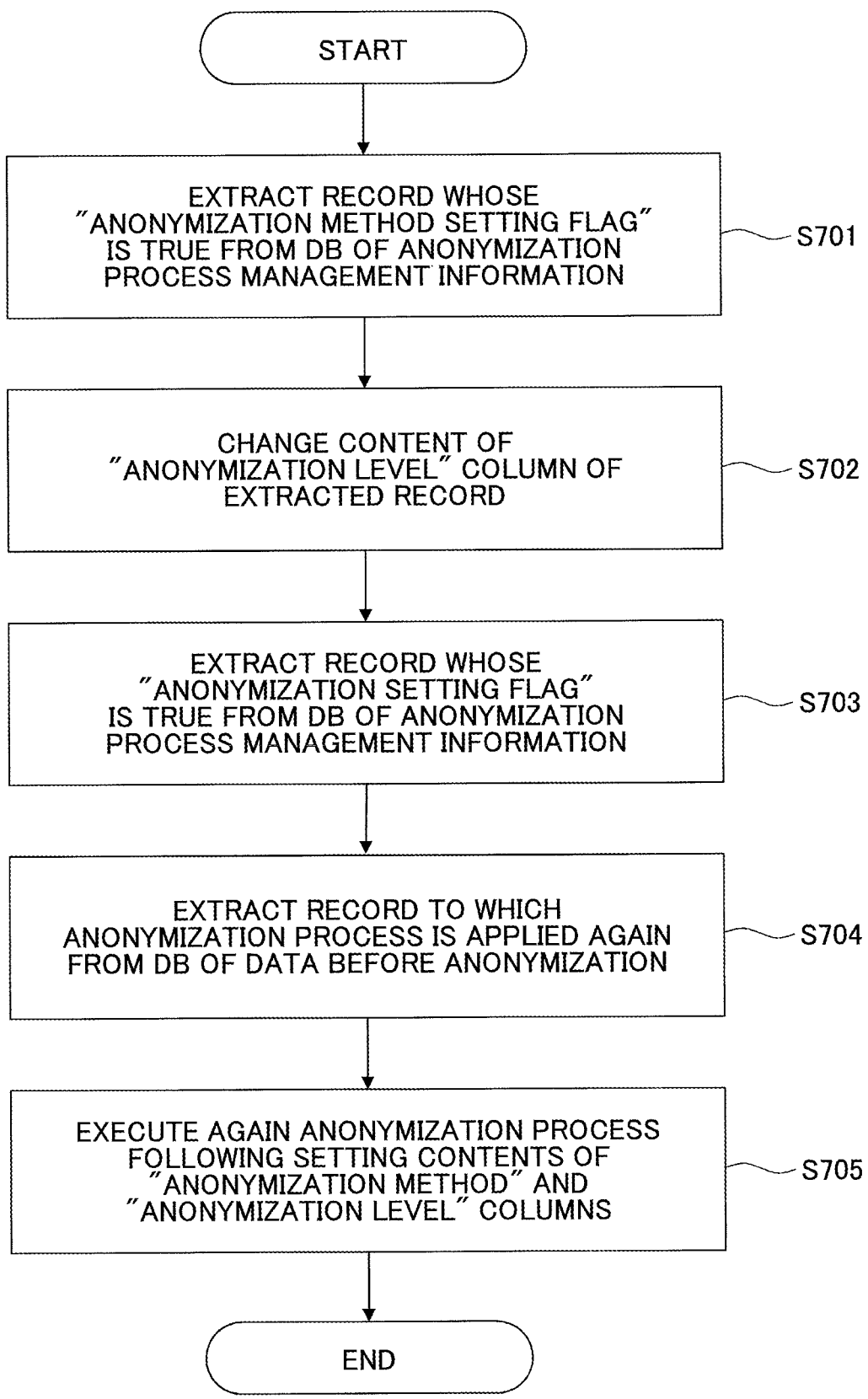
FIG. 14 is a diagram illustrating an example of processing steps in a case of changing the degree of generalization in an anonymization process.

FIG. 14 is a diagram illustrating an example of processing steps in a case of changing the degree of generalization in an anonymization process. Using FIG. 14, processing steps will be described in a case where the machine learning unit 204 adjusts the degree of generalization based on teacher data, and the anonymization processing unit 205 executes the anonymization process again.

At Step S701, the machine learning unit 204 extracts all records having the "anonymization method setting flag" column set to TRUE from the DB of anonymization process management information.

At Step S702, the machine learning unit 204 changes the content of the "anonymization level" column of all the extracted records into the content corresponding to the degree of generalization after adjustment. Also, the machine learning unit 204 indicates the change of the content of the "anonymization level" column to the anonymization processing unit 205.

At Step S703, the anonymization processing unit 205 extracts all records whose "anonymization setting flags" is TRUE from the DB of anonymization process management information.

At Step S704, the anonymization processing unit 205 extracts all items of data before anonymization corresponding to all the records extracted at Step S703 from the DB of data before anonymization.

At Step S705, for each of all the items of data before anonymization found at Step S704, the anonymization processing unit 205 executes the anonymization process again, according to the setting contents of the "anonymization method" and "anonymization level" columns of the anonymization process information corresponding to each item of the data before anonymization. Also, the anonymization processing unit 205 writes the contents of the columns of the data before anonymization to which the anonymization process has been applied, over the record of the data after anonymization corresponding to the data before anonymization among the DB of data after anonymization.

Here, specific examples of the processing steps of Step S701 through Step S705 will be described. For example, assume that the data before anonymization is represented by the data before anonymization illustrated in FIG. 6A, and data after anonymization is represented by the data after anonymization illustrated in FIG. 10A. Assume also that among the anonymization process management information in FIG. 8, the machine learning unit 204 has changed the anonymization level of the present address into "present address": "delete chome (city block) and further details" at the processing step of Step S702. In this case, at the processing step of Step S705, the anonymization processing unit 205 generates a present address column ("1-chome XY Adachi, Tokyo") in which details following the chome found in the present address column of the data before anonymization ("1-11-101 XY Adachi, Tokyo") are deleted, and writes the generated data over the present address column of the data after anonymization illustrated in FIG. 10A.

(Data Deleting Steps)

The anonymization processing unit 205 compares the present date and time with each of the "generation date and time" of each item of the anonymization process management information stored in the DB of anonymization process management information, to confirm whether data exists that has not been output as the output data (data that does not satisfy the k-anonymity within a retention time) even after time set as a retention term of real-time definition information has passed.

If the difference between the "generation date and time" of the anonymization process management information and the present date and time is over the retention term of the real-time definition information, the anonymization processing unit 205 determines that data after anonymization has not come to satisfy the k-anonymity in the retention term. If having determined that the data after anonymization has not come to satisfy the k-anonymity in the retention term, the anonymization processing unit 205 deletes the data after anonymization, and the data before anonymization and the anonymization process management information corresponding to the data after anonymization from the DB of data before anonymization, the DB of data after anonymization, and the DB of anonymization process management information, respectively.

Note that instead of comparing the "generation date and time" with the present date and time, for example, if the number of records accumulated in the temporary storage unit 201 exceeds a predetermined threshold, the anonymization processing unit 205 may delete the data before anonymization, the data after anonymization, and the anonymization process management information, from the DB of data before anonymization, the DB of data after anonymization, and the DB of anonymization process management information, respectively, in order of the generation date and time starting with oldest.

(Machine Learning Step)

The machine learning unit 204 adjusts the degree of generalization based on teacher data received from the external system or the like, or teacher data received from the output determination unit 206. The machine learning unit 204 may have the user refer to the teacher data, to adjust the degree of generalization following a command from the user, or may automatically adjust the degree of generalization based on the teacher data.

For teacher data whose "k-anonymity criterion conformity flag" is FALSE, the machine learning unit 204 adjusts the degree of generalization in a direction in which the values of personal information items become coarser (in a direction in which the degree of generalization becomes higher). For teacher data whose "k-anonymity criterion conformity flag" is TRUE, the machine learning unit 204 adjusts the degree of generalization in a direction in which the values of personal information items become more specific (in a direction in which the degree of generalization becomes lower).

Note that the machine learning unit 204 may not adjust the degree of generalization every time when receiving teacher data; alternatively, for example, the unit adjusts the degree of generalization in a direction in which the values of personal information items become coarser (in a direction in which the degree of generalization becomes higher) if the teacher data whose "k-anonymity criterion conformity flag" is FALSE increases, and adjusts the degree of generalization in a direction in which the values of personal information items become more specific (in a direction in which the degree of generalization becomes lower) if the teacher data whose "k-anonymity criterion conformity flag" is TRUE increases.

Note that a direction in which the values of personal information items become coarser means changing a setting of, for example, "present address": "delete chome (city block) and further details" into a setting of "present address": "delete city, ward, town, village, and further details". Also, a direction in which the values of personal information items become more specific means changing a setting of, for example, "present address": "delete city, ward, town, village, and further details" into a setting of "present address": "delete chome (city block) and further details".

<Effects>

As described above, the anonymization processing device 10 according to the embodiment executes an anonymization process to input data input from an external system or the like, and if satisfying the k-anonymity, outputs the anonymized output data. Accordingly, the anonymization processing device 10 according to the embodiment can anonymize, in real time, data being input continuously, while guaranteeing the anonymity.

As described above, the anonymization processing device 10 according to the embodiment executes machine learning based on teacher data representing whether the anonymized data satisfies the k-anonymity, so that the degree of generalization can be changed. Being different from a system that executes anonymization by batch processing, the anonymization processing device 10 according to the embodiment cannot identify in advance a total number of records to be anonymized. Therefore, there is a likelihood that the output data is continuously output in a direction in which the degree of generalization is higher compared with the system that executes anonymization by batch processing. Therefore, the anonymization processing device 10 according to the embodiment adjusts the degree of generalization in a direction in which the degree of generalization becomes lower for teacher data whose "k-anonymity criterion conformity flag" is TRUE, and adjusts the degree of generalization in a direction in which the degree of generalization becomes higher for teacher data whose "k-anonymity criterion conformity flag" is FALSE. Consequently, the anonymization processing device 10 according to the embodiment can output data to which the anonymization process has been applied, by an optimal degree of generalization.

Supplementary Description of Embodiment

Note the present invention described above is not limited to the embodiments; various modifications and improvements can be made within the scope of the present invention.

The flowcharts described as above in the embodiments may have a sequence of steps changed as long as no contradiction arises.

All or a part of the embodiments as stated above may be implemented by a program. This program may be stored in a storage medium.

Note that in the embodiments, the anonymization processing unit 205 is an example of a processing unit. The temporary storage unit 201 is an example of a first storage unit. The anonymization pattern DB storage unit 207 is an example of a second storage unit. The data after anonymization is an example of anonymized data. The k-anonymity is an example of an anonymity index. The degree of generalization is an example of a degree of abstraction.

The present patent application claims priority based on Japanese patent application No. 2015-013504, filed on Jan. 27, 2015, and the entire contents of Japanese patent application No. 2015-013504 are incorporated herein by reference.

LIST OF REFERENCE SYMBOLS 10 anonymization processing device
201 temporary storage unit
202 setting information storage unit
203 input unit
204 machine learning unit
205 anonymization processing unit
206 output determination unit
207 anonymization pattern DB storage unit

The invention claimed is:

1. An anonymization processing device that anonymizes input data and outputs anonymized output data, comprising:
processing circuitry configured to
receive the input data;
anonymize the input data, to generate anonymized data corresponding to the input data that has been anonymized;
store the anonymized data in a first memory;
generate a plurality of anonymization patterns for determining anonymity based on anonymized data items,
store the anonymization patterns in a second memory,
wherein in a case where each of the information items included in the anonymized data stored in the first memory is equivalent to each of the information items included in at least one of the anonymization patterns, respectively, the processing circuitry generates and outputs the output data from the anonymized data, and
in a case where each of the information items included in the anonymized data stored in the first memory is not equivalent to each of the information items included in at least one of the anonymization patterns stored in the second memory, the processing circuitry obtains an anonymity index, and where a plurality of anonymized data items stored in the first memory satisfy the anonymity index, the processing circuitry generates and outputs a plurality of output data items corresponding to the anonymized data items, respectively, and deletes the anonymized data items from the first memory.

2. The anonymization processing device as claimed in claim 1, wherein the processing circuitry determines that the anonymity index is satisfied in a case where at least a predetermined number of the anonymized data items exist that have equivalent respective information items included in the anonymized data items stored in the first memory.

3. The anonymization processing device as claimed in claim 1, wherein the processing circuitry deletes the anonymized data stored in the first memory at a timing according to a predetermined condition.

4. The anonymization processing device as claimed in claim 3, wherein the predetermined condition is an elapsed time after the input data corresponding to the anonymized data was received by the processing circuitry, or when a number of records that can be stored in the first memory exceeds a predetermined threshold.

5. An anonymization method executed by an anonymization processing device that anonymizes input data and outputs anonymized output data, the method comprising:
receiving the input data;
anonymizing the input data, to generate anonymized data corresponding to the input data that has been anonymized;
storing the anonymized data in a first memory; and
generating a plurality of anonymization patterns for determining anonymity based on anonymized data items, and storing the anonymization patterns in a second memory,
wherein in a case where each of the information items included in the anonymized data stored in the first memory is equivalent to each of the information items included in at least one of the anonymization patterns, the method includes respectively generating and outputting the output data from the anonymized data, and
in a case where each of the information items included in the anonymized data stored in the first memory is not equivalent to each of the information items included in at least one of the anonymization patterns stored in the second memory, the method includes obtaining an anonymity index, and where a plurality of anonymized data items stored in the first memory satisfy the anonymity index, the method includes respectively generating and outputting a plurality of output data items corresponding to the anonymized data items, respectively, and deleting the anonymized data items from the first memory.

6. A non-transitory computer readable medium that stores a program for causing an anonymization processing device to execute a process of anonymizing input data and outputting anonymized output data, the process comprising:
receiving the input data;
anonymizing the input data, to generate anonymized data corresponding to the input data that has been anonymized;
storing the anonymized data in a first memory; and
generating a plurality of anonymization patterns for determining anonymity based on anonymized data items, and storing the anonymization patterns in a second memory,
wherein in a case where each of the information items included in the anonymized data stored in the first memory is equivalent to each of the information items included in at least one of the anonymization patterns, the method includes respectively generating and outputting the output data from the anonymized data, and
in a case where each of the information items included in the anonymized data stored in the first memory is not equivalent to each of the information items included in at least one of the anonymization patterns stored in the second memory, the method includes obtaining an anonymity index, and where a plurality of anonymized data items stored in the first memory satisfy the anonymity index, the method includes respectively generating and outputting a plurality of output data items corresponding to the anonymized data items, respectively, and deleting the anonymized data items from the first memory.

* * * * *